United States Patent [19]

Yamamoto et al.

[11] Patent Number: 5,718,833
[45] Date of Patent: Feb. 17, 1998

[54] FLUORINE-BASED MAGNETIC FLUID

[75] Inventors: Yasushi Yamamoto, Tsukuba; Yoshiyuki Takeishi, Tsuchiura; Yutaka Kouda; Tomoko Minagawa, both of Tsukuba; Takao Kanno, Tokyo, all of Japan

[73] Assignee: NOK Corporation, Tokyo, Japan

[21] Appl. No.: 784,693

[22] Filed: Jan. 15, 1997

[30] Foreign Application Priority Data

Jan. 16, 1996 [JP] Japan ................... 8-023055

[51] Int. Cl.$^6$ ....................... H01F 1/44
[52] U.S. Cl. ................. 252/62.52; 252/62.54
[58] Field of Search ................ 252/62.52, 62.54

[56] References Cited

U.S. PATENT DOCUMENTS 3,784,471  1/1974  Kaiser ..................... 252/21

*Primary Examiner*—Melissa Bonner
*Attorney, Agent, or Firm*—Barnes & Thornburg

[57] ABSTRACT

A fluorine-based magnetic fluid, which comprises (A) fine magnetic particles as dispersed in (D) a perfluoropolyether base oil represented by the following general formula:

$$F[CF(CF_3)CF_2O]mRf$$

where Rf is a perfluoroalkyl group, by means of (B) a salt of perfluoroether carboxylic acid represented by the following general formula:

$$F[CF(CF_3)CF_2O]nCF(CF_3)COOM$$

where M is an alkali metal or an ammonium group, and (C) amide compounds of perfluoroether carboxylic acid represented by the following general formula:

$$F[CF(CF_3)CF_2O]pCF(CF_3)CONH(CH_2)qNH_2,$$

$$F[CF(CF_3)CF_2O]pCF(CF_3)CONH(CH_2CH_2NH)rH \text{ or}$$

$$F[CF(CF_3)CF_2O]pCF(CF_3)CONH(CH_2CH_2NH)rCOCF(CF_3)[OCF_2CF(CF_3)]pF$$

has a high affinity of the fine magnetic particles toward the perfluoropolyether base oil and is effectively used as a sealing material for vacuum apparatus.

12 Claims, No Drawings

FLUORINE-BASED MAGNETIC FLUID

BACKGROUND OF THE INVENTION

1. Field of the Invention

The present invention relates to a fluorine-based magnetic fluid, and more particularly to a fluorine-based magnetic fluid comprising fine magnetic particles as dispersed in a perfluoropolyether base oil.

2. Description of Related Art

U.S. Pat. No. 3,784,471 discloses a fluorine-based magnetic fluid comprising surfactant-adsorbed, fine ferrite particles as dispersed in a perfluoropolyether base oil, where perfluoropolyether carboxylic acid represented by the following general formula:

$$F[CF(CF_3)CF_2O]_mCF(CF_3)COOH$$

where m is an integer of 3 to 50, or its ammonium salt, etc. is used as the surfactant adsorbed on fine ferrite particles.

However, mere dispersion of such perfluoropolyether carboxylic acid surfactant-adsorbed, fine ferrite particles in the perfluoropolyether base oil has a poor dispersibility and a considerably large amount of poorly dispersed fine particles in the base oil, resulting in a considerable decrease not only in the magnetic fluid yield, but also in saturation magnetization of the resulting magnetic fluids, that is, poor practical applicability, as shown in Comparative Examples which follow. Furthermore, the above-mentioned US Patent discloses that the dispersibility is poor when the m value of the perfluoropolyether carboxylic acid or its salts is smaller.

SUMMARY OF THE INVENTION

An object of the present invention is to provide a fluorine-based magnetic fluid having a higher affinity of fine magnetic particles toward a perfluoropolyether base oil and an effective application as a sealing material for vacuum apparatus, etc.

According to the present invention, there is provided a fluorine-based magnetic fluid, which comprises (A) fine magnetic particles as dispersed in (D) a perfluoropolyether base oil by means of (B) a salt of perfluoroether carboxylic acid represented by the following general formula:

$$F[CF(CF_3)CF_2O]_nCF(CF_3)COOM$$

where M is an alkali metal or an ammonium group; and n is an integer of 1 to 100, and (C) amide compounds of perfluoroether carboxylic acid, represented by the following general formulae:

$$F[CF(CF_3)CF_2O]_pCF(CF_3)CONH(CH_2)_qNH_2,$$

$$F[CF(CF_3)CF_2O]_pCF(CF_3)CONH(CH_2CH_2NH)_rH \text{ or}$$

$$F[CF(CF_3)CF_2O]_pCF(CF_3)CONH(CH_2CH_2NH)_rCOCF(CF_3)$$
$$[OCF_2CF(CF_3)]_pF,$$

where p is an integer of 1 or more, preferably an integer of 4 to 50; q is an integer of 2 to 20; and r is an integer of 1 to 6.

DETAILED DESCRIPTION OF THE INVENTION

Fine magnetic particles for use in the present invention are generally fine ferrite particles, prepared by any appropriate methods, preferably by a coprecipitation method having advantages of controlling their purity and particle size, particularly their productivity. The preferable fine ferrite particles prepared by the coprecipitation method include, for example, fine particles of magnetite ($Fe_3O_4$), nickel ferrite ($NiO.Fe_2O_3$), manganese ferrite ($MnO.Fe_2O_3$), cobalt ferrite ($CoO.Fe_2O_3$), nickel-zinc ferrite ($Ni.ZnO.Fe_2O_3$), manganese-zinc ferrite ($Mn.ZnO.Fe_2O_3$), cobalt-zinc ferrite ($Co.ZnO.Fe_2O_3$), etc.

Besides, fine particles of such a metal as iron, manganese, nickel, cobalt, etc. or their borides, nitrides, carbides, etc. or furthermore fine particles of alloys of these metals with at least one of such other metals as magnesium, alminum, zinc, copper, niobium, molybdenum, gallium, indium, zirconium, cadmium, tin, etc. or their borides, nitrides, carbides, etc. can be also used as fine magnetic particles.

Generally, fine magnetic particles have a high hydrophilic property and accordingly undergo coagulation as such in a base oil, resulting in a failure to form a magnetic fluid. Thus, it is necessary to make the surfaces of fine magnetic particles have a higher affinity toward a base oil thereby preventing their coagulation. Compounds for use to enhance the affinity toward a base oil and prevent the coagulation must have preferably a fluorophilic group and a polar group having a strong adsorbability to ferrites in one molecule at the same time. In view of the necessity for a long chain having some elasticity to prevent coagulation of fine particles and a good solubility or dispersibility in a solvent, compounds having a perfluoroether group as a fluorophilic group are selected.

In the present invention, a salt of perfluoroether carboxylic acid having the above-mentioned general formula has been ultimately selected from these viewpoints. The salt of perfluoroether carboxylic acid can be obtained by hydrolysis of an alkyl ester of carboxylic acid derived from a hexafluoropropene oxide oligomer having a repetition unit n of 1 to 100, preferably 4 to 20, by an aqueous solution of sodium hydroxide, potassium hydroxide, ammonia or the like. Preferable upper limit to 20 in the repetition unit n is so selected that, when n is above 20, the resulting magnetic fluid has poor characteristics (viscosity, etc.).

As mentioned above, the dispersibility remains poor only with the salt of perfluoroether carboxylic acid, and accordingly at least one of the above-mentioned three amide compounds of perfluoroether carboxylic acid is used together with the salt of perfluoroether carboxylic acid in the present invention. The three amide compounds of perfluoroether carboxylic acid can be readily obtained by a method as described in Examples which follow, where α,ω-diaminoalkane having 2 to 20 carbon atoms, preferably 8 to 12 carbon atoms, is used in reaction with hexafluoropropene oxide oligomer carboxylic acid or its alkyl ester. Below 2 carbon atoms, the chain length is too short to prevent the coagulation, whereas above 20 carbon atoms the chain length is too long to obtain better viscosity characteristics of the resulting magnetic fluid.

The above-mentioned limit ranges for p, q or r in the general formulae of these three amide compounds of perfluoroether carboxylic acid are selected in the present invention on the ground that outside the limit ranges no better characteristics of the resulting magnetic fluid (e.g. higher dispersibility and lower viscosity) can be obtained.

The present magnetic fluid can be prepared by dispersing fine magnetic particles in a perfluoropolyether base oil in the presence of the salt of perfluoroether carboxylic acid and the amide compounds of perfluoroether carboxylic acid. The salt of perfluoroether carboxylic acid is used in an amount of about 10 to abut 100 parts by weight, preferably about 20 to abut 50 parts by weight, per 100 parts by weight of fine magnetic particles. The amide compounds of perfluoroether carboxylic acid are used in an amount of about 0.1 to abut 50 parts by weight, preferably about 1 to about 20 parts by weight, per 100 parts by weight of perfluoropolyether base oil. These salt and amide compounds of perfluoroether carboxylic acid can be added to the perfluoropolyether base oil at the same time or successively in any order.

Perfluoropolyether base oil represented by the following general formula:

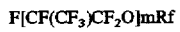

F[CF(CF$_3$)CF$_2$O]mRf where Rf is a perfluoroalkyl group, preferably a perfluoroalkyl group having 1 to 3 carbon atoms; and m is an integer of 1 or more, preferably 10 to 50 (on average), can be used in the present invention. Practically, commercially available perfluoropolyether base oil such as BARRIERTA series, trademark of a product made by NOK Klüber K.K., Japan, etc. can be used.

Dispersion treatment can be carried out by the ordinary method using a homogenizer, a ball mill, ultrasonic wave application, etc. A dispersion can be more readily prepared when a fluorinated organic solvent such as Fluorinert FC-72 (trademark of a product made by Sumitomo-3M K.K., Japan) is used at the same time. In that case the organic solvent is distilled off after the preparation of the dispersion. Then, the dispersion is subjected to centrifuge to remove poorly dispersed fine particles therefrom, whereby a magnetic fluid can be obtained.

By using a salt of perfluoroether carboxylic acid and amide compounds of perfluoroether carboxylic acid together in preparation of a fluorine-based magnetic fluid comprising fine magnetic particles as dispered in a perfluoropolyether base oil, a magnetic fluid of good dispersion can be obtained. The fluorine-based magnetic fluid thus obtained is effective for minimizing changes in vacuum degree and torque, when used as a sealing material for a vaccum apparatus with a shaft, etc.

PREFERRED EMBODIMENTS OF THE INVENTION

The present invention will be described in detail below, referring to Examples and Comparative Examples.

EXAMPLE 1

A mixture consisting of the following Components (A) to (D) was subjected to a dispersion treatment under application of ultrasonic waves for 24 hours, whereby 39.9 g of fluorine-based magnetic fluid was obtained:

| | | |
|---|---|---|
| (A) Coprecipitation process fine material perticles: (particle size: 90Å) | 4 | g |
| (B) F[CF(FC$_3$)CF$_2$O]nCF(CF$_3$COONa (n: 8 on average): | 1 | g |
| (C) F[CF(CF$_3$)CF$_2$O]pCF(CF$_3$)CONH(CH$_2$)$_{12}$NH$_2$: (P: 15 on average) | 5 | g |
| (D) Perfluoropolyether base oil: (BARRIERTA J100V) | 30 | g |

The Component (B) was obtained by dropwise adding 50 g (0.03 moles) of methyl ester of hexafluoropropene oxide oligomer carboxylic acid (n: 8 on average) to an aqueous solution containing 5 g (0.13 moles) of sodium hydroxide in 100 ml of water at 80° C. at a trickling rate of 1 ml/min. with stirring, continuing the stirring for 5 hours while keeping that temperature, then leaving the reaction solution to stand for cooling, adding about 50 g of sodium chloride thereto, and recovering precipitated white solid by filtration, followed by drying, dissolution into methanol, filtration and distilling-off of methanol under reduced pressure [amount of the product: 48.0 g (yield: 96.4%)].

The Component (C) was obtained by adding 3 g (14.8 millimoles) of 1,12-diaminododecane to 10 g (3.7 millimoles) of methyl ester of hexafluoropropene oxide oligomer carboxylic acid (p: 15 on average), stirring mixture at 120° C. for 5 hours, then leaving the mixture to stand for cooling, and then adding 100 ml of methanol and 100 ml of a fluorine-based solvent (Fluorinert FC72) to dissolve the reaction mixture, followed by separation of Fluorinert FC72 layer in a separating funnel and distilling-off of Fluorinert FC72 under reduced pressure [amount of the product: 10.5 g (yield: 97.0%)].

The fluorine-based magnetic fluid thus obtained was filled into a space formed between a shaft having 15 mm in diameter and a seal assembly of pole piece-permanent magnet-pole piece as inserted along the shaft to make a vacuum seal, and then the vacuum seal was placed in a vacuum seal-evaluating apparatus and put into a continuous operation under such conditions of 0.01 Torr and 1,000 rpm for 500 hours to determine the vacuum degree and torque. It was found that there was no change in the vacuum degree with the percent torque change being less than 1%.

EXAMPLE 2

In Example 1, the same amount of the following amide compound was used as the Component (C) in place of the amide compound of Example 1, and the same results were obtained.

F[CF(CF$_3$)CF$_2$O]pCF(CF$_3$)CONH(CH$_2$)$_8$NH$_2$ (p: 15 on average)

The Component (C) of Example 2 was obtained in the same procedure for obtaining the Component (C) as in Example 1, except that 2 g (14.8 millimoles) of 1,8-diaminooctane was used in place of 1,12-diaminododecane [amount of the product: 10.2 g (yield: 97%)]:

EXAMPLE 3

In Example 1, the same amount of the same compound (though n is 15 on average) was used as Component (B) in place of the Component (B) of Example 1, and the same results were obtained. The Component (B) for use in Example 3 was prepared in the same manner for preparing Component (B) as in Example 1, except that 80 g (0.03 moles) of methyl ester of hexafluoropropene oxide oligomer carboxylic acid (n: 15 on average) was used [amount of the product: 78.8 g (yield: 97%)].

EXAMPLE 4

In Example 1, the same amount of the following amide compound was used as the Component (C) in place of the Component (C) of Example 1 to prepare a fluorine-based magnetic fluid:

F[CF(CF$_3$)CF$_2$O]pCF(CF$_3$)CONH(CH$_2$CH$_2$NH)$_9$H (p: 15 on average)

The magnetic fluid thus obtained was subjected to measurement of vacuum degree and torque in the same manner as in Example 1. It was found that there was no change in the vacuum degree with the percent torque change being less than 5%. The Component (C) for use in Example 4 was prepared in the same manner for preparing Component (C) as in Example 1, except that 3.5 g (14.8 millimoles) of pentaethylenehexamine was used in place of 1,12-diaminododecane [amount of the product: 10.4 g (yield: 96.0%)].

EXAMPLE 5

In Example 4, the same amount of the following amide compound was used as the Component (C) in place of the Component (C) of Example 4 and the same results were obtained:

F[CF(CF$_3$)CF$_2$O]pCF(CF$_3$)CONH(CH$_2$CH$_2$NH)$_4$H (p: 15 on average)

The Component (C) for use in Example 5 was prepared in the same manner for preparing Component (C) as in Example 1, except that 2.8 g (14.8 millimoles) of tetraethylenepentamine was used in place of 1,12-diaminododecane [amount of the product: 10.2 g (yield: 96.0%)].

EXAMPLE 6

In Example 4, the same amount of the same compound (though n is 15 on average) was used as the Component (B) in place of the Component (B) of Example 4 and the same results were obtained. The Component (B) for use in Example 6 was prepared in the same manner as in Example 3.

EXAMPLE 7

In Example 1, the same amount of the following bisamide compound was used as the Component (C) in place of the Component (C) of Example 1 to prepare a fluorine-based magnetic fluid:

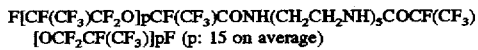

F[CF(CF$_3$)CF$_2$O]pCF(CF$_3$)CONH(CH$_2$CH$_2$NH)$_5$COCF(CF$_3$)
[OCF$_2$CF(CF$_3$)]pF (p: 15 on average)

The magnetic fluid thus obtained was subjected to measurement of vacuum degree and torque. It was found that there was no change in the vacuum degree with the percent torque change being less than 5%.

The Component (C) was prepared by adding 0.4 g (1.8 millimoles) of pentaethylenehexamine (product made by Tokyo Kasei K.K., Japan) to 10 g (3.7 millimoles) of methyl ester of hexafluoropropene oxide oligomer carboxylic acid (p: 15 on average), stirring the mixture at 120° C. for 5 hours, and then adding 100 ml of a fluorine-based solvent (Fluorinert FC72) thereto to dissolve the reaction mixture, followed by separation of Fluorinert FC72 layer in a separating funnel and distilling-off of Fluorinert FC72 under reduced pressure [amount of the product: 10.0 g (yield: 98.0%)].

EXAMPLE 8

In Example 7, the same amount of the following bisamide compound was used as the Component (C) in place of the Component (C) of Example 7 and the same results were obtained:

F[CF(CF$_3$)CF$_2$O]pCF(CF$_3$)CONH(CH$_2$CH$_2$NH)$_4$COCF(CF$_3$)
[OCF$_2$CF(CF$_3$)]pF (p: 15 on average)

The Component (C) for use in Example 8 was prepared in the same manner for preparing Component (C) as in Example 7 except that 0.3 g (1.85 millimoles) of tetraethylenepentamine was used in place of pentaethylenehexamine [amount of the product: 9.9 g (yield: 98.0%)].

EXAMPLE 9

In Example 7, the same amount of the same compound (though n is 15 on average) was used as the Component (B) in place of the Component (B) of Example 7 and the same results were obtained. The Component (B) for use in Example 9 was prepared in the same manner for preparing Component (B) as in Example 3.

COMPARATIVE EXAMPLE 1

In Example 1, the Component (C) was not used at all. Dispersibility of fine magnetic particles was so poor that no magnetic fluid was obtained.

COMPARATIVE EXAMPLE 2

In Example 3, the Component (C) was not used at all. A magnetic fluid was obtained, but the vacuum degree was lowered with the percent torque change being more than 10%.

What is claimed is:

1. A fluorine-based magnetic fluid, which comprises (A) fine magnetic particles as dispersed in (D) a perfluoropolyether base oil represented by the following general formula:

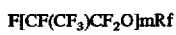

F[CF(CF$_3$)CF$_2$O]mRf where Rf is a perfluoroalkyl group; m is an integer of 1 or more, by means of (B) a salt of perfluoroether carboxylic acid represented by the following general formula:

F[CF(CF$_3$)CF$_2$O]nCF(CF$_3$)COOM where M is an alkali metal or an ammonium group: and n is an integer of 1 to 100, and (C) an amide compound of perfluoroether carboxylic acid represented by the following general formula:

F[CF(CF$_3$)CF$_2$O]pCF(CF$_3$)CONH(CH$_2$)qNH$_2$ where p is an integer of 1 or more and q is an integer of 2 to 20.

2. A fluorine-based magnetic fluid according to claim 1, wherein the fine magnetic particles are fine ferrite particles.

3. A fluorine-based magnetic fluid according to claim 1, wherein about 10 to about 100 parts by weight of the salt of perfluoroether carboxylic acid is used per 100 parts by weight of the fine magnetic particles.

4. A fluorine-based magnetic fluid according to claim 1, wherein about 0.1 to about 50 parts by weight of the amide compound of perfluoroether carboxylic acid is used per 100 parts by weight of the perfluoropolyether base oil.

5. A fluorine-based magnetic fluid, which comprises (A) fine magnetic particles as dispersed in (D) a perfluoropolyether base oil represented by the following general formula:

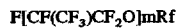

F[CF(CF$_3$)CF$_2$O]mRf where Rf is a perfluoroalkyl group; m is an integer of 1 or more, by means of (B) a salt of perfluoroether carboxylic acid represented by the following general formula:

$$F[CF(CF_3)CF_2O]_nCF(CF_3)COOM$$

where M is an alkali metal or an ammonium group; and n is an integer of 1 to 100, and (C) an amide compound of perfluoroether carboxylic acid represented by the following general formula:

$$F[CF(CF_3)CF_2O]_pCF(CF_3)CONH(CH_2CH_2NH)_rH$$

where p is an integer of 1 or more and r is an integer of 1 to 6.

6. A fluorine-based magnetic fluid according to claim 5, wherein the fine magnetic particles are fine ferrite particles.

7. A fluorine-based magnetic fluid according to claim 5, wherein about 10 to about 100 parts by weight of the salt of perfluoroether carboxylic acid is used per 100 parts by weight of the fine magnetic particles.

8. A fluorine-based magnetic fluid according to claim 5, wherein about 0.1 to about 50 parts by weight of the amide compound of perfluoroether carboxylic acid is used per 100 parts by weight of the perfluoropolyether base oil.

9. A fluorine-based magnetic fluid, which comprises (A) fine magnetic particles as dispersed in (D) a perfluoropolyether base oil represented by the following general formula:

$$F[CF(CF_3)CF_2O]_mRf$$

where Rf is a perfluoroalkyl group; m is an integer of 1 or more, by means of (B) a salt of perfluoroether carboxylic acid represented by the following general formula:

$$F[CF(CF_3)CF_2O]_nCF(CF_3)COOM$$

where M is an alkali metal or an ammonium group; and n is an integer of 1 to 100, and (C) a bisamide compound of perfluoroether carboxylic acid represented by the following general formula:

$$F[CF(CF_3)CF_2O]_pCF(CF_3)CONH(CH_2CH_2NH)_rCOCF(CF_3)\\ [OCF_2CF(CF_3)]_pF$$

where p is an integer of 1 or more and r is an integer of 1 to 6.

10. A fluorine-based magnetic fluid according to claim 9, wherein the fine magnetic particles are fine ferrite particles.

11. A fluorine-based magnetic fluid according to claim 9, wherein about 10 to abut 100 parts by weight of the salt of perfluoroether carboxylic acid is used per 100 parts by weight of the fine magnetic particles.

12. A fluorine-based magnetic fluid according to claim 9, wherein about 0.1 to about 50 parts by weight of the bisamide compound of perfluoroether carboxylic acid is used per 100 parts by weight of the perfluoropolyether base oil.

* * * * *